(12) United States Patent
Israel et al.

(10) Patent No.: US 9,714,508 B2
(45) Date of Patent: Jul. 25, 2017

(54) STRUCTURES FORMED WITH SHEET MATERIAL CONFIGURED WITH AT LEAST ONE SOUND ABSORBING LAYER

(71) Applicants: Tara A. Israel, East Hampton, NY (US); Bonnie S. Schnitta, East Hampton, NY (US)

(72) Inventors: Tara A. Israel, East Hampton, NY (US); Bonnie S. Schnitta, East Hampton, NY (US)

( * ) Notice: Subject to any disclaimer, the term of this patent is extended or adjusted under 35 U.S.C. 154(b) by 0 days.

(21) Appl. No.: 14/996,218

(22) Filed: Jan. 14, 2016

(65) Prior Publication Data

US 2016/0201318 A1 Jul. 14, 2016

Related U.S. Application Data

(60) Provisional application No. 62/103,363, filed on Jan. 14, 2015.

(51) Int. Cl.
| | |
|---|---|
| *E04B 1/86* | (2006.01) |
| *E04B 1/82* | (2006.01) |
| *G10K 11/168* | (2006.01) |
| *E04B 1/84* | (2006.01) |

(52) U.S. Cl.
CPC .......... *E04B 1/8209* (2013.01); *E04B 1/8409* (2013.01); *G10K 11/168* (2013.01)

(58) Field of Classification Search
CPC ........ E04B 1/86; E04B 1/8209; E04B 1/8409; G10K 11/168

USPC .......................................................... 181/290
See application file for complete search history.

(56) References Cited

U.S. PATENT DOCUMENTS

| | | | | |
|---|---|---|---|---|
| 4,942,938 A | * | 7/1990 | Wiegel | E04H 1/12 181/295 |
| 8,136,626 B1 | * | 3/2012 | Aliev | F24F 13/24 181/198 |
| 8,646,571 B2 | * | 2/2014 | Aliev | H04M 1/19 181/198 |
| 8,978,816 B2 | * | 3/2015 | Slotznick | E04H 15/18 181/30 |
| 2003/0116379 A1 | * | 6/2003 | Khambete | B32B 11/04 181/290 |
| 2006/0090832 A1 | * | 5/2006 | Allison | B32B 3/10 156/72 |
| 2012/0070609 A1 | * | 3/2012 | Poppe | B32B 5/16 428/95 |
| 2012/0321849 A1 | * | 12/2012 | Richardson, III | B64C 1/40 428/138 |

* cited by examiner

*Primary Examiner* — Forrest M Phillips
(74) *Attorney, Agent, or Firm* — John F. Vodopia

(57) ABSTRACT

A structure configured with an inner, sound limited or reduced volume is formed with a frame and a sheet material arranged about the frame to form and enclose the sound limited or reduced volume. The sheet material includes a base layer and a layer of sound-absorbing material provided on or integral with the base layer and the sound limited or reduced volume includes a form of egress that in an open state allows for the sound entry to and exit from the sound limited or reduced volume and in a closed state limits sound entry to and exit from the sound limited or reduced volume.

13 Claims, 3 Drawing Sheets

STRUCTURES FORMED WITH SHEET MATERIAL CONFIGURED WITH AT LEAST ONE SOUND ABSORBING LAYER

CROSS-REFERENCE TO RELATED APPLICATIONS

This application derives the benefit of the filing date of U.S. Provisional Patent Application No. 62/103,633, filed Jan. 14, 2015, the content of which provisional application is incorporated herein by reference.

BACKGROUND OF THE INVENTION

The present invention is directed to a structure formed with sheet material that includes at least one sound absorbing layer in order to limit an amount of unwanted sound (e.g., noise) entering a space or volume internal to the structure and/or an amount of sound generated within the internal space or volume and transmitted through the sound absorbing layer to outside the structure.

There are a number of temporary or mobile structures designed for a range of needs, be it a tent for camping or a play fort for children. A tent or teepee, for example, may be constructed with purpose specific materials, so a camper can select a climate appropriate tent or a play fort can be made that is soft to the touch of a child.

For example, U.S. Pat. No. 8,978,816 discloses a sound-limiting acoustic shell by way of a hanging acoustic canopy. The intent of U.S. Pat. No. 8,978,816 is to create a portable acoustic shell that optimizes a musician's ability to hear what other players are performing under that same canopy. It also has in its design the ability to project sound so that it is better heard by an audience. Additionally, the absorbing material of this invention is designed to bring the decay time to a level that reduces the noise in the structure. Whereas this will make the speech or music sound better within the invention, a better sound is not the main goal of the NRC and STC of the invention, it is just a consequence.

SUMMARY OF THE INVENTION

The present invention overcomes the shortcomings of known arts, such as those mentioned above, for achieving a quantifiable level of desired or required quietude inside or outside a structure that can be portable if necessary.

To that end, the present invention provides a structure constructed with a sheet material formed that at least partially includes a sound absorbing layer to limit the amount of sound able to pass through the portion into and out of the structure formed therewith. The sheet material may be any type of material that is flexible, such as cloth, including weaves, non-woven material and knits, bendable aluminum or metal, and organic or inorganic polymer sheets, such as vinyl, plastic sheeting, tarps or any material that can be formed into the desired structure shape.

The sound absorbing material may be configured to absorb sound energy when sound waves collide with it, or pass by it and inhibits sound waves that attempt to pass through the material, as opposed to reflecting the sound energy on the inside of the sheet material. For example, LUMITEX® is a sound absorbing material manufactured by or for distributed end/or sold by SoundSense LLC, Wainscott, N.Y. that also provides SIC value when properly configured. Depending on materials of construction and configuration the structure will offer anything from the reduction of isolated frequencies to virtual sound isolation.

One version of the structure intended for noise reduction has only the sound absorbing material that is located on the inside of the sheet material adhered to or otherwise arranged to be integral with at least a part of a surface of the sheet material. The sound absorbing material, e.g., a sheet thereof, is adhered to the base sheet material by any means known to a person of ordinary skill in the art for adhering, attaching, sewing or applying one material to a surface or portion of a base sheet. The base sheet material may be cloth, a polymer, or any material chosen to accommodate the goals and aesthetics of the application.

Another version of the structure intended for noise reduction has the sound absorbing material that is located on the inside of the sheet material in addition to another layer that is a barrier layer, such as a loaded vinyl. Both materials are adhered to, or otherwise arranged to be, integral with each other. If necessary for aesthetic reasons, at least a part of the sheet material surface is a material befitting its application, such as a soft or patterned fabric, by any means known to a person of ordinary skill in the art for adhering, attaching, sewing or applying one material to a surface or portion of a surface of a sheet material comprising any synthetic or natural material, such as cloth or polymer.

The resulting sheet material with the sound absorbing layer, or sound absorbing layer with a barrier layer, is preferably flexible so that it may be configured to function as a boundary to unwanted sound, separating an environment in which there is an undesirable sound level (such as the sound of traffic or talking) from an environment where a lower ambient sound level is desired (or required), such as an internal environment substantially enclosed with the sheet material soundproofed with the sound absorbing layer.

Of course, the internal environment enclosed with the sheet material covered with the sound absorbing layer also operates to absorb sound generated in the internal environment so that noise level therein is lowered substantially.

In an embodiment, the invention includes a structure configured with an inner sound-limited or sound-reduced volume that is formed with a frame and a sheet material arranged about the frame to form and enclose sound-limited or sound-reduced volume. The sheet material has a base layer and a layer of sound-absorbing material provided on or integral with the base layer. The sound-limited or sound-reduced volume includes an entrance (means of egress) that in an open state allows for the sound entry to and exit from the sound-limited or sound-reduced volume and, in a closed state limits sound entry to and exit from the sound-limited or sound-reduced volume.

The frame of the structure can be constructed like a teepee, tent frame, or other shape that can be framed where the sheet material is part of the fabric configuration attached to the frame. The means of egress is preferably a flap. The flap is formed with a layer of sound absorbing material. In a variation, the sheet material includes two or more layers of sound absorbing material and may include a barrier. When a high level of acoustic separation is required, the flap or teepee entrance area is sufficiently long enough to act as a muffler. Accordingly, the two layers of sound absorbing material surround a base layer. The layer of sound-absorbing material is detachably connected to the base layer. The portion of the sheet material with the sound absorbing material, that transforms into the sound-limited or sound-reduced volume, not only minimizes sound entry but also minimizes an amount of sound exiting the inner volume, i.e., operates to soundproof the inner volume. The sheet material and sound-absorbing material used for the sound-limited or sound-reduced volume is preferably the same as the material from which the entrance is formed.

BRIEF DESCRIPTION OF THE DRAWINGS

The invention will be described in conjunction with the following drawings in which reference numerals designate like elements and wherein:

FIG. 5B Depicts a material sheet formed to include a layer of sound barrier material sandwiched between at least two inner material layers and at least two outer material layers.

DETAILED DESCRIPTION OF THE INVENTION

The following is a detailed description of the example embodiments of the invention as depicted in the accompanying drawings. The example embodiments are presented in detail as to clearly communicate the invention and are designed to make such embodiments obvious to a person of ordinary skill in the art. However, the amount of detail offered is not intended to limit the anticipated variations of embodiments; on the contrary, the intention is to cover all modifications, equivalents, and alternatives falling within the spirit and scope of the present invention, as defined by the appended claims.

Figure 1A:
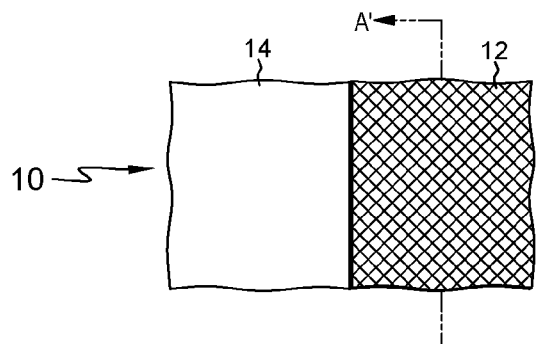
FIG. 1A Depicts a plan view of a surface of a sound attenuating sheet material formed by adhering sound absorbing or sound absorbing with a barrier material to approximately one half of one surface of the sheet of material.
Figure 1B:
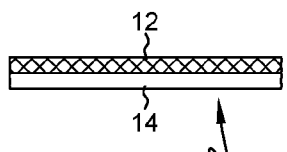
FIG. 1B Depicts a side cutaway view of the sheet material along the cut A-A' depicted in FIG. 1A.

FIG. 1A depicts a plan view of the surface of a sound attenuating sheet material 10 formed by adhering sound absorbing or sound absorbing and barrier material 12 to approximately one half of one surface of the sheet of material 14. FIG. 1B shows a side cutaway view of sheet 10 along the cut A-A' depicted in FIG. 1A.

Figure 2:
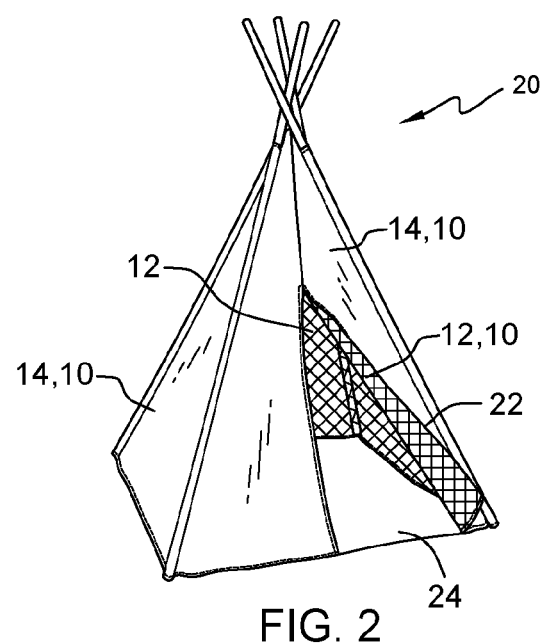
FIG. 2 Depicts a teepee structure that is formed with the sound attenuating sheet material including the sound absorbing layer or sound absorbing and barrier layer.
Figure 3:
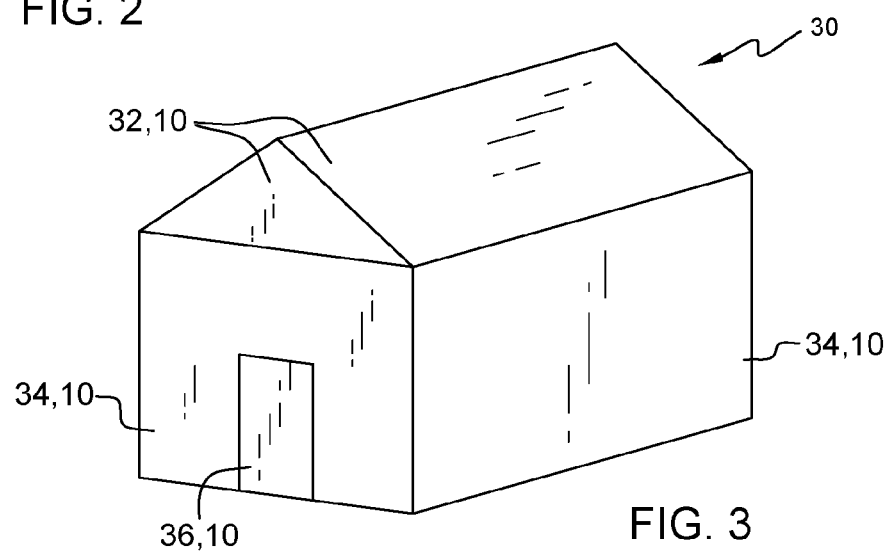
FIG. 3 Depicts a house or tent structure that is formed with the sound attenuating sheet material including the sound absorbing layer or sound absorbing and barrier layer.

FIGS. 2, 3 and 4 depict examples of structures that can be formed with the sound attenuating sheet material 10 formed with the sound absorbing layer or sound absorbing and barrier layer 12.

Whereas the STC and NRC of the sheet material is important to the design of any of the structures, it can vary according to the application. That is, in some applications it is more important that the inside of the structure have a comfortable sound decay time and only slightly reduce the outside noise entering the structure. There are other applications where a slight noise reduction from one side of the structure to the other is acceptable, but it is most important that the structure be light and easily portable. This is when the NRC criterion is more important than that of the STC. Other instances it is critical that the noise entering or exiting through the sheet material structure is significantly reduced if not eliminated to the opposite side of the structure. This is when the STC criterion becomes critical. Other instances the entrance needs to be open for easy access or airflow without an acoustically treated air flow chamber and the design of the flap or muffler type entrance tunnel then needs to match the criterion of the NRC and STC just stated.

FIG. 2 depicts a teepee 20 constructed with sound attenuating sheet material 10. The teepee is shown with a flap 22 in an open state, which flap would otherwise cover opening 24 in a closed state. When closed, some portion of the sound generated inside the teepee will not be transmitted to outside the teepee because of the sound attenuating sheet material 10. Likewise, the sound attenuating sheet material 10 limits sounds generated outside the teepee from passing through to enter the internal volume of the teepee. Perhaps as importantly, the sound generated inside the teepee is attenuated and softened inside the teepee to outside the teepee by the sound attenuating sheet material 10 (formed with the sound absorbing material or sound absorbing and barrier material 12 on some portion if not all of one surface).

The FIG. 2 construction is a basic tent design, e.g., an igloo-like tent, with fiberglass, wood, or metal supporting structure such that the tent/teepee is easily stored or transported in a very compact form. For that matter, a smaller tent or teepee-style structure constructed according to the inventive principles would be ideal for children to play in and not disturb those outside of the tent. The support poles for such a smaller structure, which would likely not require the portability of a tent, could be made of material other than that used for conventional tent poles, such as bamboo poles. The only requirement is that the poles for the smaller tent or teepee be sufficiently sturdy to withstand play, but light enough it can be disassembled and reassembled easily. All forms of the tent/teepees, or other small shaped structures would be constructed to allow for the airflow necessary which is required to "soundproof" a space. An acoustic viewing window could also be part of the structure.

A larger tent-like structure of any shape formed with the sound-attenuating sheet material 10 including a layer of sound absorbing material could accommodate an adult or a number of adults. Similar design and concept, but with the intended use being for adults to study, practice music, meditate, nap or talk on the phone without major disruption to those around them (and vice versa). The sound-attenuating sheet material 10 enables formation of structures enveloping an internal environment that "tunes" the noise down to make it a tolerable sound level, but does not eliminate noise entirely. Consequently, children could play freely inside the structure and an adult could work or have a phone conversation in the same room without having to compete with the volume of the children, but still have the ability to supervise the activity.

FIG. 3 depicts a house-like structure 30, configured around a shape-giving frame (not shown) covered with sound attenuating sheet material 10 (such as that depicted in FIGS. 1A and 1B). As shown, the sound attenuating sheet material 10 (with the sound absorbing material on the inside surface) is covering the roof 32, the sides 34 and even the door 36, soundproofing the inside environment from the outside environment and vice versa, when the door is closed. Such a structure is intended only as an example embodiment, and does not need to have the walls 34 and roof as shown. For that matter, even a door may not be necessary, where a flap of the sound attenuating sheet material 10 or unraveling of the sound attenuating sheet material 10 could function to allow entry and exit from the structure 30 and act as an acoustical muffler. In such a case, the structure could be a tent, "lean to," cabana, hut, etc., and preferably portable with application for both indoor and outdoor usage, without limitation.

The structure built with the sound attenuating sheet material 10 formed with the sound absorbing material 12 on one surface also may be used advantageously to create modular sound environments. That is, the sheet/sound absorbing material 10/12, may form an outer surface of a multi-ply sheet, an inner surface of a multi-ply sheet or just a material sheet that separates an environment external to the modular sound environment and internal to the modular sound environment. Such modular sound environments allow for multiple activities of different volumes to "co-habitate" in the same space, by the inherent property of attenuating sound present therein without requiring a permanent wall that retracts or folds into or up against a wall or ceiling, etc.

Additionally, the sound attenuating sheet material 10 formed with the sound absorbing material 12 on one surface could be used to construct a small or medium enclosure (i.e., form an acoustic enclosure) designed to go over a dog cage. An opening, resembling something like an igloo opening, could be included in the covering to not only allow for air to flow to the dog, but also to serve as a muffler for the dog barking that is exiting the enclosure. By time the sound exits the opening it is reduced in dB level so that it is no longer disturbing to anyone in the vicinity. This second muffler entrance area height would depend on the size of the dog, as well as the noise reduction requirements. Often the opening, or even the full enclosure, can be just a simple arch shape.

An application to apply sound absorbing material 12 to the sheet 14 for sound attenuating can be a little different than that required for soundproofing. Design can include a full seam to a floor panel, etc., to create a more effective acoustic treatment, such as would be necessary when used for covering equipment, such as generators or computer fans.

Figure 4A:
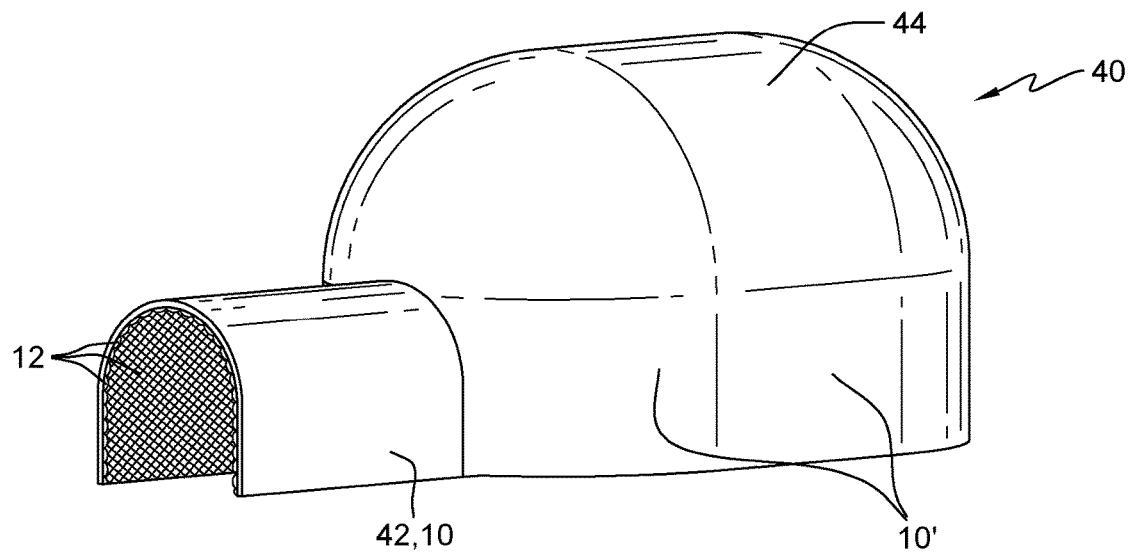
FIG. 4 Depicts an igloo-like structure formed with the sound attenuating sheet material including the sound absorbing layer or sound absorbing and barrier layer.
Figure 4B:
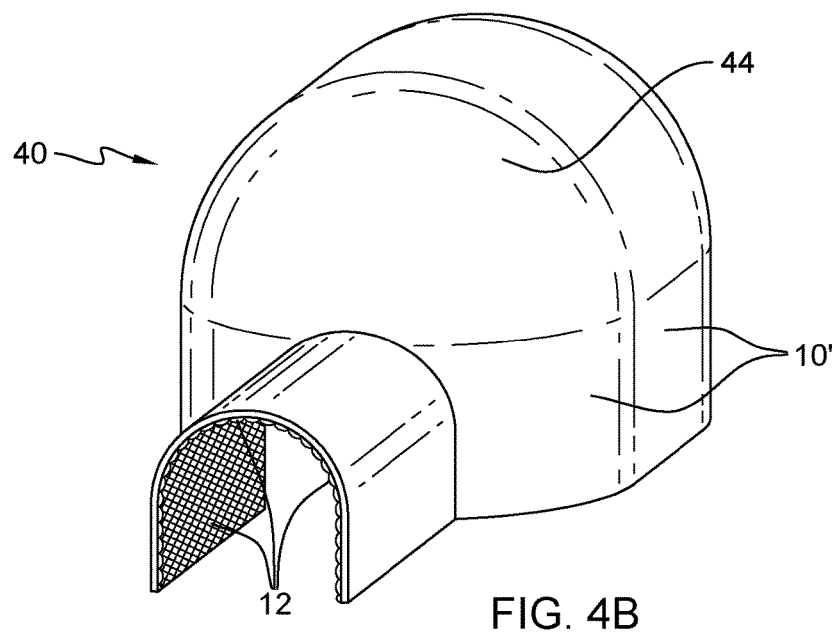

FIGS. 4A and 4B depict side and side (front) perspective views of an igloo-type structure or tent including attenuating sheet material 10 formed with a sound absorbing layer 12 adhered to or integral with a base material sheet 14. The igloo-type structure 40 is configured with a curved entrance 42, attached to a larger area 44 functioning as a work or sleeping area, that functions as a muffler, attenuating sound traveling through the length of the muffler (between the surface of the larger area 44 and the opening in the muffler 42, as shown) whether the sound is traveling in or out. The sheet material 10' covering the larger area 44 may comprise sheet material 10, or a variation on sheet material 10, or a sheet material that does not include the sound-absorbing material 12.

It is advantageous that the structures constructed include the attenuating sheet material 10 formed with a sound absorbing layer 12 adhered to or integral with a base material sheet 14 are portable, so that a sound controlled or sound reduced space can be arranged in almost any environment and in particular, spaces surrounded by enclosures created to have a very short life span, like a tent, lean-to, igloo, cabana, changing area or napping/sleeping area.

Figure 5A:
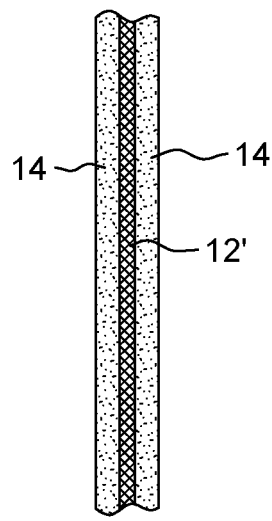
FIG. 5A Depicts a material sheet formed to include a layer of sound absorbing material sandwiched between an inner material lager and an outer material layer.
Figure 5B:
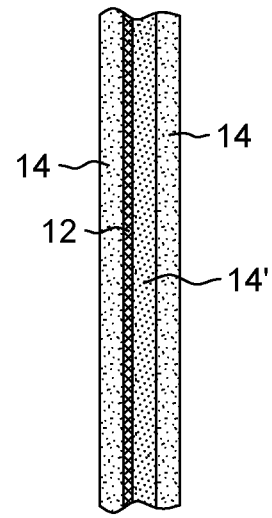
FIG. 5B Depicts a material sheet formed to, include a layer of sound barrier material sandwiched between an inner material layer and at least two outer material layers.
Figure 5C:
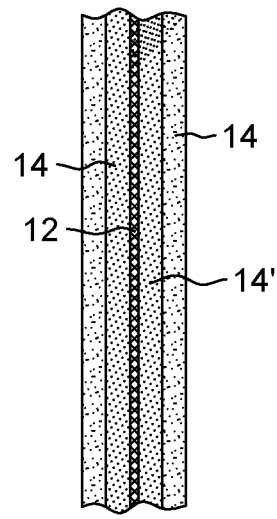

FIG. 5A shows a material sheet formed with any number of layers of materials, including a layer of sound absorbing material 12', The layers may be said to be in sheets, for example, with an inner material layer 14 (formed for its look and feel and outer material layer 14 surrounding the layer (or multiple layers) of sound absorbing material operation a quasi-barrier layer 12', as shown. The sound absorbing layer 12' (FIG. 5A) may be 1 to 6 or more layers of Lumitex material or other absorbers such as glass, foam or fiberglass. The outer material layer 14 defines the look and feel of the material sheets, for example, by its softness or ability to be written on. FIG. 5B depicts the embodiment of FIG. 5A, including an additional outer material layer 14, as shown, and wherein the sound absorbing layer 12' is replaced by a sound barrier layer 12. FIG. 5C depicts the embodiment of FIG. 5A including at least 2 inner layers of material 14 and at least two outer layers of material 14, as well as a barrier layer 12, replacing sound absorbing layer 12' (FIG. 5A).

Another application would be to have an additional layer of material that inhibits radio frequency (RF) and similar frequency wave energy in combination with the attenuating sheet material. While the embodiment was described with only a single noise or sound absorbing layer, the sheet material also may include multiple noise or sound absorbing layers on a base layer without deviating from the scope and spirit of the invention. The second noise absorbing layer can function as a decoupler for potential low frequency noises. The sound waves emitted from any source proximate the user (or a portion thereof) are absorbed by the noise absorbing layer before it enters any reduced sound compartment, like a small space for speaking on a cell phone enclosed by the sheet portion comprising the structure (enclosure). With such a construction, a suitable sound transmission loss is achieved. The outer, inner or both noise absorbing layers preferably are made of a high NRC rated material, where "NRC" stands for noise reduction coefficient and represents the average amount of sound absorbed by the material. The NRC rating typically ranges from 0.01 to 1.0. NRC ratings above 1 (e.g., 1.03) are also possible. The higher the NRC rating, the greater the sound absorption of the material. The noise or sound absorbing layer(s) is/are chosen based upon the characteristics of the particular mechanism or noise to be absorbed.

Various materials are contemplated. In particular, the material forming the noise or sound absorbing layer(s) is/are chosen for sound absorbing qualities and possibly the ability to operate as a heat insulator to enhance the ability to use the structure as a proper shelter. As such, the noise attenuation layer can differ from that forming the base layer. The layer may also be formed from a closely woven textile-like material made of any suitable material provided the material has suitable sound absorbing properties and withstands a predetermined temperature. A suitable adhesive can be used to secure the sound or noise absorbing layer to a base material layer. When multiple noise absorbing layers are provided, the layers can be formed from either the same material or a different material. Alternatively, the noise absorbing layer can be connected to a base or barrier layer when the garment is formed.

In an embodiment, for example, the invention provides a structure configured with an inner, substantially sound-limited or sound-reduced volume. The structure comprises a frame and material arranged about the frame to form and enclose the sound-limited or sound-reduced volume. The material may be formed as a sheet (weave, knit, sprayed, extruded, etc.). At least a portion of the sheet material includes sound-absorbing material; the sound-limited or sound-reduced volume includes an entrance that in an open state allows for sound entry to and exit from the sound-limited or sound-reduced volume and in a closed state limits sound entry to and exit from the sound-limited or sound-reduced volume. In one form, the material sheet embodies a base layer and wherein the sound-absorbing material is provided on or integral with at least one portion of the base layer. Alternatively, the material sheet embodies a base layer, the sound-absorbing material embodies a sheet and wherein the sheet of sound-absorbing sheet is provided on the at least one portion of the base layer.

The frame can be an igloo, teepee, tent, or habitable structure frame and the sheet material can be an igloo skin, a tent fabric, a teepee fabric, or habitable structure material. The entrance comprises an opening that is removably covered with a flap. The flap includes sound absorbing material. In a variation, the sheet material includes two or more layers of sound absorbing material in the at least one portion. For that matter, the two layers of sound absorbing material surround the base layer.

The base layer is a natural or synthetic fabric. The sound-absorbing material is detachably connected to the base layer. The sheet material defining the sound-limited or sound-reduced volume minimizes an amount of sound entering the sound-limited or sound-reduced volume from outside the structure and an amount of sound exiting the sound-limited or sound-reduced volume from inside the structure. The sheet material defining sound-limited or sound-reduced volume is the same as the material forming the entrance is the same.

As will be evident to persons skilled in the art, the foregoing detailed description and figures are presented as examples of the invention, and that variations are contemplated that do not depart from the fair scope of the teachings and descriptions set forth in this disclosure. The foregoing is not intended to limit what has been invented, except to the extent that the following claims so limit that.

What is claimed is:

1. A structure configured with an inner, substantially sound-limited or sound-reduced volume, the structure comprising:
   a frame; and
   material arranged about the frame to form and enclose the sound-limited or sound-reduced volume;
   wherein the material comprises a base layer and a layer of sound-absorbing material provided on at least one portion of the base layer;
   wherein the layer of sound absorbing material is attached to or integral with the base layer; and
   wherein the sound-limited or sound-reduced volume includes an entrance that in an open state allows for sound entry to and exit from the sound-limited or sound-reduced volume and in a closed state limits sound entry to and exit from the sound-limited or sound-reduced volume.

2. The structure of claim 1, wherein the base layer is a synthetic fabric.

3. The structure of claim 1, wherein the layer of sound-absorbing material is provided on or integral with the base layer in its entirety.

4. The structure of claim 1, where the frame is an igloo, teepee, tent, or habitable structure frame and wherein the chcet material is an igloo skin, a tent fabric, a teepee fabric, or habitable structure material.

5. The structure of claim 1, where the entrance comprises an opening that is removably covered with a flap.

6. The structure of claim 5, wherein the flap includes a base layer of material that is surrounded on both opposing sides by at least one layer of sound absorbing material.

7. The structure of claim 1, wherein the base layer is a natural fabric.

8. The structure of claim 1, wherein the material embodying the base layer and the sound-absorbing layer that surrounds the sound-limited or sound-reduced volume minimizes an amount of sound entering the sound-limited or sound-reduced volume from outside the structure and an amount of sound exiting the sound-limited or sound-reduced volume from inside the structure.

9. A structure configured with an inner, substantially sound-limited or sound-reduced volume, the structure comprising:
   a frame; and
   material arranged on or about the frame to form and enclose the sound-limited or sound-reduced volume;
   wherein the material comprises a base layer and two layers of sound-absorbing material;
   wherein the sound-limited or sound-reduced volume includes an entrance that in an open state allows for sound entry to and exit from the sound-limited or sound-reduced volume and in a closed state limits sound entry to and exit from the sound-limited or sound-reduced volume;
   wherein the two layers of sound absorbing material are provided on or integral with opposing sides of the base layer in at least one portion of the base layer; and
   wherein the entrance is covered by a flap formed by the material in the closed state and wherein the flap does not cover the entrance in the open state.

10. The structure of claim 9, wherein the material comprising the base layer and the two layers of sound-absorbing material surrounding the sound-limited or sound-reduced volume is the same as the material forming the entrance.

11. A structure configured with an inner, substantially sound-limited or sound-reduced volume, the structure comprising:
    a frame; and
    material arranged about the frame to form and enclose the sound-limited or sound-reduced volume;
    wherein the material comprises a base layer;
    wherein at least one portion of the base layer includes a first layer of sound-absorbing material provided on or integral with at least one portion of the base layer;
    wherein the sound-limited or sound-reduced volume includes an entrance that in an open state allows for sound entry to and exit from the sound-limited or sound-reduced volume and in a closed state limits sound entry to and exit from the sound-limited or sound-reduced volume; and
    wherein a flap comprising the material covers the entrance in closed state, is positioned away from the volume in an open state and, in the open state, forms an entrance area long enough to act as a muffler.

12. The structure of claim 11, wherein the first layer of sound-absorbing material is provided on or integral with the base layer in its entirety.

13. The structure of claim 12, further comprising a second layer of sound-absorbing material provided on or integral with the base layer, on a side of the base layer opposing the first layer of sound-absorbing material.

* * * * *